United States Patent [19]

Yazawa et al.

[11] 4,387,990
[45] Jun. 14, 1983

[54] CHEMICAL ANALYSIS SLIDE FRAME ASSEMBLY

[75] Inventors: Kenichiro Yazawa; Masao Kitajima; Asaji Kondo, all of Asaka, Japan

[73] Assignee: Fuji Photo Film Co. Ltd., Kanagawa, Japan

[21] Appl. No.: 247,677

[22] Filed: Mar. 26, 1981

[30] Foreign Application Priority Data

Mar. 28, 1980 [JP] Japan ............................. 55/41787[U]

[51] Int. Cl.³ ...................... G01N 21/01; G01N 21/27
[52] U.S. Cl. ...................................... 356/244; 422/58; 422/102
[58] Field of Search .................. 356/244; 422/58, 102, 422/104; 350/536

[56] References Cited

U.S. PATENT DOCUMENTS 3,690,836  9/1972  Buissiere et al. .................... 422/102

Primary Examiner—Vincent P. McGraw
Attorney, Agent, or Firm—Sughrue, Mion, Zinn, Macpeak and Seas

[57] ABSTRACT

A chemical analysis slide frame assembly including first and second slide frames each having an opening whose area is smaller than the area of a chemical analysis film inserted therein and a third slide frame disposed between the first and second slide frames. The third slide frame has an opening which is adapted to receive the chemical analysis film and is shaped so as to substantially prevent the displacement of the chemical analysis film. The third slide frame has a thickness which is equal to or larger than the thickness of the chemical analysis film. The side wall of the opening in the first slide frame has a small optical reflection factor, preferably is dark so as to provide a small optical reflection factor.

31 Claims, 10 Drawing Figures

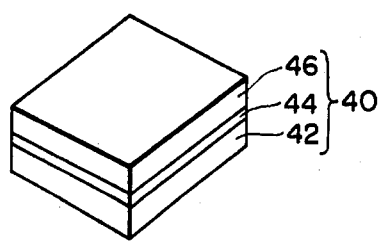
FIG. 1
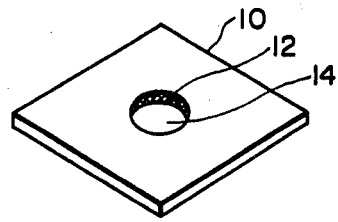
FIG. 2
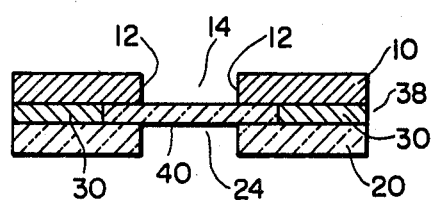
FIG. 3
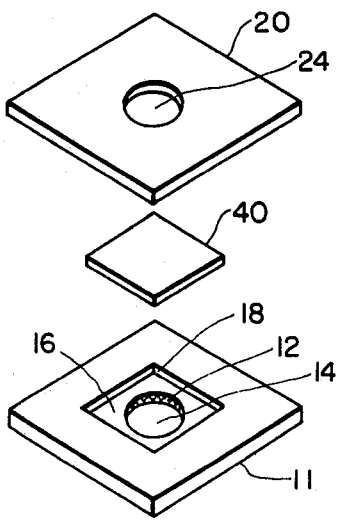
FIG. 4
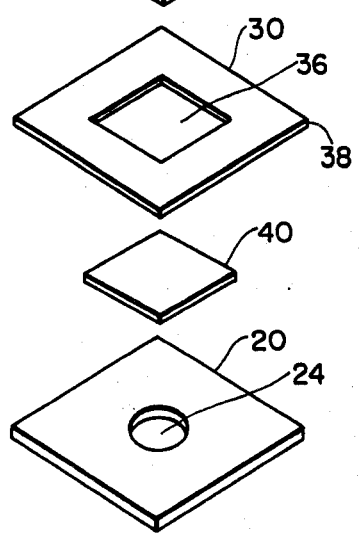

CHEMICAL ANALYSIS SLIDE FRAME ASSEMBLY

BACKGROUND OF THE INVENTION

The present invention relates to slide frame assemblies for receiving chemical analysis films. More particularly, the invention relates to the structure of a slide frame assembly into which a chemical analysis film for analyzing the components of a liquid sample in an optical density measurement is inserted. The invention further relates to the structure of a chemical analysis slide which is prepared by inserting a chemical analysis film in such a slide frame assembly.

Chemical analysis films or sheets for aqueous solution samples (hereinafter referred to as "chemical analysis films" when applicable), and especially new multi-layer type chemical analysis film used for quickly analyzing a component or components in a body fluid such as blood or urine, are generally well known in the art. Films or sheets of the general type to which the invention pertains are disclosed, for example, in U.S. Pat. Nos. 3,992,158, 3,983,005, 4,042,335 and 4,066,403, and Published Unexamined Japanese patent application No. 164,356/80 (corresponding to U.S. co-pending application Ser. No. 157,737 filed on June 9, 1980).

The structure of such a conventional chemical analysis film 40 is such that, as shown in FIG. 1, a single or plural reagent layers 44 can be placed on a transparent support 42 and a porous spread layer 46 placed on the single or plural reagent layers 44. Then, these layers are formed into a single unit so that they may not be peeled apart. Alternatively, only the porous spreading layer 46 and the single or plural reagent layers 44 form the chemical analysis film 40.

A liquid sample dropped onto the porous spreading layer of of chemical analysis film spreads uniformly through the porous spread layer 46 and enters the reagent layer for chemical reaction as a result of which the sample is colored or its color is changed. The degree of this change in color can be determined by observing or measuring the optical density through the reagent layer or the transparent support.

In this determination, a component in the liquid sample reacts with the reagent in the reagent layer. In this reaction, the coloring reaction of an organic reagent in water is often utilized. The chemical analysis film has a significant feature that the analyzing operation is of the dry type. The chemical analysis film is supplied after being inserted into a cartridge such as that disclosed in Japanese Laid-Open Utility Model Application No. 162294/1979 or into a slide frame which is similar to a conventional slide frame for a transparent positive picture photographic film. For quantitative analysis, the optical density of the chemical analysis slide in which the chemical analysis film has been inserted is measured by a chemical analyzer as disclosed in U.S. Pat. Nos. 4,119,381 and 4,152,390 and in U.S. co-pending application Ser. No. 212,009 filed on Dec. 1, 1980 so that the component to be detected is subjected to quantitative analysis.

These conventional slide frames are specifically intended as slide frames for transparent positive picture films which have been used for slide frames for receiving chemical analysis films. The conventional slide frames are not always sufficient for the strict or accurate measurement of optical density values. More specifically, the conventional slide frames are disadvantageous in the following points. First, usually the slide frame is white or light grey or light-colored and the surface of the slide frame is glossy or semi-glossy. Therefore, when a light beam is applied to the slide frame for an optical density measurement, rays scattered from the light beam and rays scattered and reflected from the chemical analysis film, reflected from the surface of the slide frame and from the side walls of the opening in the slide frame, enter the photometric path or the photometric unit in the chemical analyzer and cause errors in the measurement of optical density. In addition, the configuration and size of the opening in the slide frame are not always suitable for the measurement of optical density.

Accordingly, an object of the invention is to provide a slide frame assembly for a chemical analysis film with which an optical density measurement of high accuracy can be achieved using an optical reflection method or an optical transmission method.

Another object of the invention is to provide a slide frame assembly for a chemical analysis slide, the surface of which does not scatter or reflect rays scattered from a light beam for optical density measurement or rays scattered and reflected from the chemical analysis film.

A further object of the invention is to provide a slide frame assembly for a chemical analysis slide which has the end face of an opening formed therein which does not scatter or reflect rays scattered from a light beam for optical density measurement or rays scattered and reflected from the chemical analysis film.

A still further object of the invention is to provide a slide frame assembly for a chemical analysis slide in which the surface on which a liquid sample is dropped or stuck can be readily discriminated.

SUMMARY OF THE INVENTION

Provided according to the invention is a chemical analysis slide frame assembly including first and second slide frames each having an opening whose area is smaller than the area of a chemical analysis film which the frame is adapted to receive and a third slide frame disposed between the first and second slide frames. The third slide frame has an opening which is adapted to receive the chemical analysis film and which is shaped so as to substantially prevent the displacement of the chemical analysis film. The third slide frame has a thickness which is equal to or larger than the thickness of the chemical analysis film, in which, according to the invention, the side wall of the opening in the first slide frame has a small optical reflection factor, and preferably the side wall of the opening in the first slide frame is made dark so as to provide a small optical reflection factor.

In the chemical analysis slide frame assembly as described above, according to another aspect of the invention, the first and third slide frames are formed as a single unit in advance.

Furthermore, in the chemical analysis slide frame assembly as described above, according to another aspect of the invention, the second and third slide frames are formed as a single unit in advance.

The first, second and third slide frames forming the chemical analysis slide frame assembly according to the invention are plates which remain substantially flat and are scarcely deformed. The third slide frame has a thickness which is equal to or larger than the thickness of a chemical analysis film to be inserted therein. The third slide frame is so shaped that the chemical analysis film can be inserted in its opening. In other words, the third slide frame functions as a spacer which is interposed between the first and second slide frames to prevent the displacement of the chemical analysis film on the first and second slide frames of the chemical analysis slide. Accordingly, the first and third slide frames can be formed in advance into a single unit which has a recess for receiving a chemical analysis film with the film fixedly disposed over the opening of the first slide frame. Similarly, the second and third slide frames can be formed in advance into a single unit which has a recess for receiving a chemical analysis film with the film being fixedly disposed over the opening of the second slide frame.

BRIEF DESCRIPTION OF THE DRAWINGS

FIG. 1 is a schematic diagram showing a chemical analysis film;

FIG. 2 is a schematic perspective view showing a preferred embodiment of a chemical analysis slide frame assembly according to the invention;

FIG. 3 is a schematic sectional view taken along a plane crossing the opening of a chemical analysis slide which is prepared by inserting a chemical analysis film in the assembly shown in FIG. 2 and by bonding the slide frames of the assembly;

FIG. 4 is a schematic perspective view showing another embodiment of a chemical analysis slide frame assembly according to the invention;

DESCRIPTION OF THE PREFERRED EMBODIMENTS

Figure 5:
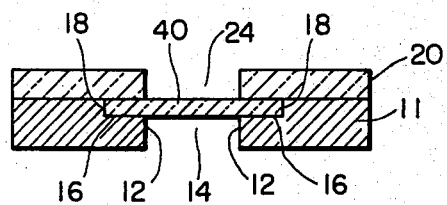
FIG. 5 is a schematic sectional view taken along a plane crossing the opening of a chemical analysis slide which is manufactured by inserting a chemical analysis film in the assembly shown in FIG. 4 and by bonding the first and second slide frames together.

Preferred embodiments of the invention will be described with reference to FIGS. 2 through 10.

FIG. 2 is an exploded perspective view showing a preferred embodiment of a chemical analysis slide frame assembly according to the invention which includes first, second and third slide frames. FIG. 3 is a schematic sectional view taken along a plane which crosses the opening of the chemical analysis slide frame assembly of FIG. 2 in which the third slide frame is bonded to the first and second frames to constitute the chemical analysis slide frame assembly and a chemical analysis film is inserted to the chemical analysis slide frame assembly. In FIGS. 2 and 3, reference numeral 10 designates a first slide frame, 14 an opening, 12 the side wall of the opening 14 with the side wall having a small optical reflection factor and preferably being dark so as to provide a small optical reflection factor, 20 a second slide frame, 24 an opening, 30 a third slide frame, 36 an opening which is so designed that its configuration and size prevent the displacement of a chemical analysis slide inserted therein, 38 the thickness of the third slide frame 3 which is equal to or slightly larger than the thickness of the chemical analysis film inserted therein, and 40 the above-described chemical analysis film.

FIG. 4 is an exploded perspective view showing another embodiment of a chemical analysis slide frame assembly according to the invention which includes first and third slide frames, which have been formed as a single unit in advance, and a second slide frame. FIG. 5 is a schematic sectional view taken along a plane which crosses the opening of the chemical analysis slide frame assembly of FIG. 4 in which a chemical analysis film is sandwiched between the first and second slide frames which are bonded together. In FIGS. 4 and 5, reference numeral 11 designates first and third slide frames which have been formed as a single unit in advance (hereinafter referred to as "a first slide frame 11 with a recess" or "a first recessed slide frame 11" when applicable), 14 an opening, 12 the side wall of the opening with the side wall having a small optical reflection factor and preferably being dark, 16 a recess whose configuration and size are so determined as to not permit the displacement of a chemical analysis film inserted therein, 18 the depth of the recess which is equal to or slightly larger than the thickness of the chemical analysis film inserted therein, 20 a second slide frame, 24 an opening, and 40 the above-described chemical analysis film. The chemical analysis slide frame assembly in FIG. 4 is composed of two slide frames, namely, the first slide frame with the recess and the second slide frame.

If the first slide frame with the recess is molded with plastic polymeric material, then the following advantages are provided. First, the chemical analysis slide frame can be manufactured at a relatively low cost. Furthermore, in manufacturing a chemical analysis slide by inserting a chemical analysis film in the chemical slide frame assembly, all that is necessary is to bond the second slide frame to the first slide frame with the recess. In addition, as the number of bonding points is few, the manufactured chemical analysis slide is rigid.

Figure 6:
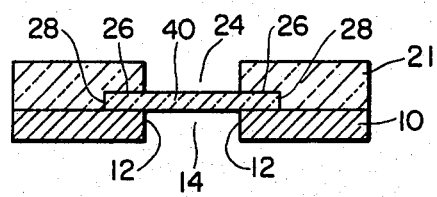
FIGS. 6 through 9 are schematic sectional views taken along planes crossing the opening of four chemical analysis slides which are fabricated by inserting chemical analysis films in four other embodiments of a chemical analysis slide frame assembly according to the invention.

FIG. 6 is a schematic sectional view of still another embodiment of a slide frame assembly of the invention taken along a plane which crosses the opening of the slide which is also manufactured by insertion of a chemical analysis film into a slide frame assembly which includes a first slide frame, and second and third slide frames which have been formed as a single unit in advance, and being bonded. In FIG. 6, reference numeral 10 designates a first slide frame, 14 an opening, 12 the side wall of the opening 14 with the side wall having a small optical reflection factor and preferably being made dark, 21 second and third slide frames which have been formed into a single unit in advance (hereinafter referred to as "a second slide frame 21 with a recess" when applicable), 24 an opening, 26 a recess whose configuration and size prevent the displacement of a chemical analysis film inserted therein, 28 the depth of the recess 26 which is equal to or slightly larger than the thickness of the chemical analysis film inserted therein, and 40 the chemical analysis film. As is apparent from the above-description, the chemical analysis slide in FIG. 6 is composed of the first slide frame and the second slide frame with the recess. Each of the chemical analysis slide frame assemblies shown in FIGS. 4 and 6 is made up of two slide frames. However, the two slide frame assemblies are different in the following point. In the slide frame assembly shown in FIG. 4, the recess for receiving a chemical analysis film is formed in the slide frame which has the opening whose side wall has a small optical reflection factor and preferably is dark. On the other hand, in the slide frame assembly shown in FIG. 6, the recess is formed in the slide frame in which such as opening is not formed.

Figure 7:
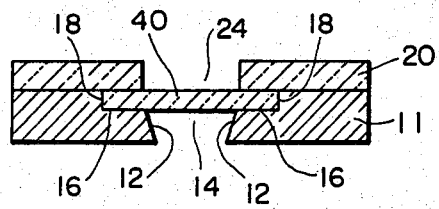
Figure 8:
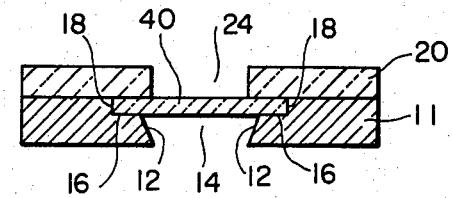

FIGS. 7 and 8 are schematic sectional views taken along planes crossing the openings of additional examples of chemical analysis slide frame assemblies according to the invention in which the side wall of an opening formed in a first slide frame is inclined and the side wall has a small optical reflection factor and preferably is made dark. Each of the chemical analysis slide frame assemblies in FIGS. 7 and 8 including a first slide frame with a recess and a second slide frame is fundamentally similar to that shown in FIG. 4. However, the slide frame assembly in each of FIGS. 7 and 8 different from that in FIG. 4 in that the side wall of the opening formed in the first slide frame is inclined. In FIGS. 4, 7 and 8, like parts are designated by like reference numerals. In the slide frame assembly shown in FIG. 7, the inner diameter of the opening in the first slide frame with the recess, which is closer to the second slide frame, is equal to the diameter of the opening in the second slide frame. Accordingly, the outer diameter of the opening in the first slide frame with the recess, which is further from the second slide frame, is smaller than the diameter of the opening in the second slide frame. In the slide frame assembly shown in FIG. 8, the outer diameter of the opening in the first slide frame with the recess, which is farther from the second slide frame, is equal to the diameter of the opening in the second slide frame, and accordingly the inner diameter of the opening in the first slide frame with the recess, which is closer to the second slide frame, is larger than the diameter of the opening in the second slide frame.

In the chemical analysis slide frame having the opening whose side wall has a small optical reflection factor and preferably is dark, rays scattered from an incident light beam for optical density measurement and rays scattered and reflected from the chemical analysis film are reflected by the side wall of the opening in the slide frame as a result of which the quantity of light entering the photometric path or the photometric unit in the chemical analyzer is greatly reduced or substantially reduced to zero. Accordingly, the optical density measurement error is greatly decreased. In the chemical analysis slide frame assembly in FIG. 7, the area of the recess can be made large. Therefore, the slide frame assembly in FIG. 7 is especially advantageous in that a chemical analysis film can be maintained satisfactorily flat therein. In goes without saying that the slide frame assemblies shown in FIGS. 7 and 8 can be modified in such a manner that the modified slide frame assemblies have a different relation between the size of the opening whose side wall has a small optical reflection factor and preferably is made dark and the size of the opening in the second slide frame.

Figure 9:
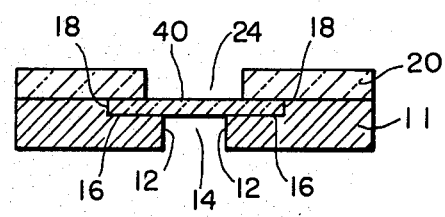

FIG. 9 is a schematic sectional view taken along a plane crossing the opening thereon of another embodiment of a chemical analysis slide frame assembly according to the invention in which the size of an opening in a first slide frame, which has a side wall which has a small optical reflection factor, and preferably is made dark, is smaller than the size of an opening formed in a second slide frame. The chemical analysis slide frame assembly in FIG. 9, including a first slide frame with a recess and a second slide frame, is fundamentally similar to that in FIG. 4. It is different only in that the size of the opening in the first slide frame with the recess is smaller than the size of the opening in the second slide frame. In FIGS. 9 and 4 or 5, like parts are designated by like reference numerals. In the chemical analysis slide frame assembly in FIG. 9, the area of the recess can be made large. Therefore, the slide frame assembly in FIG. 9 is advantageous in that a chemical analysis film can be maintained sufficiently flat therein.

In the various embodiments of a chemical analysis slide frame assembly according to the invention shown in FIGS. 4 through 9, the first slide frame having the opening whose side wall has a small optical reflection factor, and preferably is made dark so as to provide a small optical reflection factor and the third slide frame are formed as a single unit, namely, the first slide frame with the recess. In contrast to these embodiments, chemical analysis slide frame assemblies composed of a second slide frame with a recess which is obtained by forming the second slide frame and the third slide frame as a single unit and a first slide frame having an opening whose side wall has a small optical reflection factor, and preferably is made dark so as to provide a small optical reflection factor and being simply in the form of a plate with the side wall being shaped as shown in FIGS. 4 through 9, can be formed as modifications of the invention. Furthermore, the above-described embodiments of the chemical analysis slide frame assembly according to the invention can be modified in such a manner that a chemical analysis slide frame assembly includes a first slide frame with a recess and a second slide frame with a recess wherein the sum of the depths of the two recesses is equal to or slightly larger than the thickness of a chemical slide film to be inserted therein.

A very significant feature of a chemical analysis slide frame assembly according to the invention is that the side wall of the opening in the first slide frame has a small optical reflection factor, and preferably is made dark so as to provide a small optical reflection factor. In this connection, it is desirable that the entire surface of the first slide frame, which is farther from the second slide frame, or a part of the surface which is around the opening in the first slide frame, is made dark to reduce the optical reflection factor. That is, all that is required in this connection is that the side wall of the opening in the first slide frame and the region around the side wall be made dark to reduce the optical reflection factor. This eliminates the problems associated with, in measuring the optical density of a chemical analysis film, rays being scattered from the incident light beam and rays being scattered and reflected from the chemical analysis film and which are further scattered and reflected from the side wall of the opening and the part of the surface of the first slide frame which is around the opening entering the photometric path or the photometric unit in the chemical analyzer. This effect is significant especially in the case where the optical density of a chemical analysis film is measured according to principles of reflection photometry.

Figure 10:
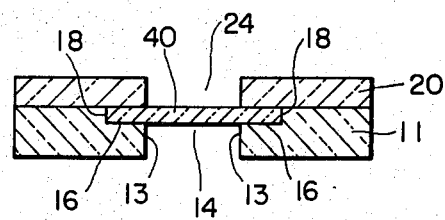
FIG. 10 is a schematic sectional view taken along a plane crossing the opening of a conventional chemical analysis slide which is prepared by inserting a chemical analysis film in a conventional chemical analysis slide frame assembly.

FIG. 10 is a schematic sectional view taken along a plane crossing the opening of an example of a conventional chemical analysis slide frame assembly which includes a first slide frame with a recess and a second slide frame. This slide frame assembly is similar in construction to that shown in FIG. 4 with the exception that the side wall of an opening in the first slide frame and the surface of the latter which is further from the second slide frame are white, light grey or light-colored. Accordingly, the reference numerals in FIG. 10 are the same as those in FIG. 4 or 5 with the exception that reference numeral 13 designates the side wall of the opening which is not dark and accordingly not having a small optical reflection factor.

The first, second and third embodiments of a slide frame, or the first slide frame with the recess and the second slide frame with the recess forming the chemical analysis slide frame assembly according to the invention can be fabricated by dye-punching a plate or sheet shaped material such as a polymer sheet, cardboard, non-woven cloth, a metal sheet or a wooden plate or by molding and, if necessary, by cutting the material thus treated. Examples of a suitable polymer are thermoplastic polymers such as polyvinyl chloride, vinyl chloride-vinylidene chloride copolymer, polyethylene, polypropylene, polystyrene, poly(methyl methacrylate), acrylonitrile-butadiene copolymer, polyester (for instance, poly(ethylen) terephthalate or bisphenol-A polycarbonate), polyamide (for instance, 6-nylon, 6,10-nylon, and 11-nylon), and cellulose ester (for instance, cellulose diacetate, cellulose triacetate, and cellulose acetate phthalate). Also suitable are thermosetting polymers such as various phenol resins and urea resins. Examples of suitable paper or cardboard are ordinary paper or cardboard made of natural pulp, paper or cardboard manufactured from synthetic polymer pulp, and paper or cardboard in which various polymers or pre-polymers are impregnated. In the case of manufacturing the slide frame by dye-punching or cutting the above-described sheet or plate shaped material, a laminate made of the sheet or plate shaped materials may be employed. Among the above-described materials, the most preferable are the thermoplastic polymers such as polyethylene, polystyrene, polypropylene, polyamide, and polyester (such as poly(ethylene terephthalate) and bisphenol-A polycarbonate).

A feature which is common to all the above-described embodiments of a chemical analysis slide frame assembly according to the invention is that the side wall (12) of the opening in the first slide frame or in the first slide frame with the recess has a small optical reflection factor, and preferably is made dark so as to provide a small optical reflection factor. This dark side wall of the opening can be obtained by various techniques. For instance, the side wall can be coated with a dark lusterless paint or dark short fiber filaments implanted in the side wall of the opening. Otherwise, the side wall of the opening can be covered with particles which are dark and have a small optical reflection factor. The slide frame itself can be made of dark polymer, paper or cardboard, and, if necessary, the side wall of the opening treated as described above, or the side wall roughened by a conventional method, or a number of fine grooves cut in the side wall. In the case where the slide frame is made of polymer, it is preferable to use a mixture which is prepared by adding a dark coloring material (carbonblack particles, graphite particles, or other dark pigment or dye, for instance) to the polymer uniformly whereby the first slide frame or the first slide frame with the recess fabricated using the mixture is dark in its entirety and accordingly has a small optical reflection factor. Furthermore, the above-described techniques of reducing the optical reflection factor can be applied to the side wall of the opening in the first slide frame or in the first slide frame with the recess which is manufactured using the polymer to which the above-described dark coloring material has been added.

The first slide frame or the first slide frame with a recess which is dark and accordingly has a small optical reflection factor is most preferable. However, the first slide frame or the first slide frame with a recess which is dark red, deep red, dark blue or deep blue and accordingly has a high optical absorptivity and low optical reflection factor is also quite acceptable.

In fabricating the second slide frame or the second slide frame with the recess, it is unnecessary to change the color of the material. Moreover, it can be manufactured using a mixture which is prepared by mixing a polymer material with a particular coloring material such as titanium oxide particles (white), barium sulfate particles (white), zinc oxide particles (white), or other coloring pigments or dyes. If the second slide frames are manufactured using mixtures which are prepared as described above, then the different colors of the slide frames can be utilized as codes for classifying chemical analysis slides (i.e. the chemical analysis films inserted therein). Furthermore, if the outer surface of the second slide frame or the second slide frame with the recess, which is farther from the chemical analysis film, is formed as a mat surface, then it is made possible to mark data thereon with an ordinary writing instrument (such as a pencil, a fountain pen, a ball-point pen, or the like) and data can be written thereon readily and positively.

The side wall of the opening in the second slide frame or in the second slide frame with the recess, or both the side wall and the outer surface which is farther from the first slide frame or the first slide frame with the recess, may have a small optical reflection factor, and preferably may be made dark so as to provide a small optical reflection factor. In this case, i.e., in order to reduce the optical reflection factor by coloring the second slide frame (or the second slide frame with the recess), the above-described technique of reducing the reflection factor by coloring the first slide frame (or the first slide frame with the recess) dark can be equally employed. The dark color of the first slide frame (or the first slide frame with the recess) may be the same as the dark color of the second slide frame (or the second slide frame with the recess) or may be different.

In the case where a chemical analysis slide is used in quantitative analysis made by reflection photometry, in order to correctly measure a reflection optical density, it is necessary for the photometric light beam to irradiate only the surface of the chemical analysis film. It has been found experimentally that if the slide frame has a high reflection factor and the diameter of the opening in the photometric surface is nearly equal to the diameter of a light beam, the measurement value of the reflection optical density will be affected by irregular reflections on the side wall of the opening in the slide frame. However, if the material and color of the first slide frame is selected so as to reduce the optical reflection factor, then the fluctuations in the measured value due to the irregular reflections from the frame can be reduced. Such a material is preferably lusterless plastic, non-gloss paper or metal or the like. It is most preferable that the color of the first slide frame be black; however, it may be red, blue or the like if it has a sufficiently high optical absorptivity.

If only the photometrically measuring surface has a deep color so that it is clearly different in color from a sample sticking surface, then the probability of occurrence of an erroneous operation in which, for instance, the sample sticking surface is mistaken for the measuring surface with the result that a sample is stuck onto the measuring surface, can be greatly reduced.

In order to increase the efficiency of a measuring operation, it is desirable that the configuration of the chemical analysis slide frame assembly be such that a variety of inspection items can be measured through the same operation or procedure. That is, it is desirable that a variety of inspection items be chemical analysis slides which have the same configuration. However, if the chemical analysis slides do have the same configuration, then the correspondence of the inspection items to the chemical analysis slides is not clearly designated and confusion may occur in selecting the inspection items or the chemical analysis slides. In order to eliminate such a difficulty, it is necessary to mark one or both sides of the slide frame assembly with a color, a pattern or a character so that its inspection item can be clearly discriminated. The discriminating of the slide frame assemblies by marking thereof is easily accomplished; however, it is disadvantageous in that it takes much time and effort to read the characters. On the other hand, discrimination of the slide frame assemblies according to the color and/or pattern marked thereon is advantageous in that the slide frame assemblies can be readily and positively discriminated. Thus, the latter technique is excellent in practice.

In bonding one of the slide frames to the other slide frame in which a chemical analysis film has been inserted, a conventional adhesive or bonding method using heat (for instance, using a heater or ultrasonic waves) may be employed. In the case where the slide frame assembly is thermoplastic polymer, it is preferable to employ a bonding method to the slide frames using ultrasonic waves because the work efficiency is thereby increased.

It is desirable that the size of the opening in the slide frame including the liquid sample sticking surface in the chemical analysis slide frame assembly according to the invention be equal to or slightly smaller than the liquid sample spreading area. If the size of the opening is much smaller than the liquid drop spreading area, then the free spreading of the liquid sample is obstructed by the presence of the slide frame with the result that the coloring is liable to be non-uniform. For instance, in the case of adhering a sample of 10 $\mu$l, it is desirable that the diameter of the opening for adhering the sample be at least 8 mm. On the other hand, in order to accurately measure the reflection optical density of a chemical analysis film, it is necessary to hold the chemical analysis film as flat as possible. Because of this, it is desirable that the diameter of the opening in the slide frame be as small as possible. The diameter of a light beam for photometry is, in general, 1 to 5 mm. Thus, the diameter of the opening of the photometric surface should be at least 5 mm. That is, with respect to the diameter of the opening of the slide frame assembly according to the invention, the necessary minimum areas of the openings on the sides of the sample adhering surface and of the reflection photometrically measuring surface are determined in accordance with the particular conditions of use.

It has been found experimentally that the diameter of the opening on the liquid sample adhering surface of the slide frame assembly should be 8 to 20 mm, preferably 8 to 15 mm, and more preferably 9 to 12 mm, and that the diameter of the opening for measuring the reflection optical density, depending on the diameter of a light beam for photometry, should in practice be 1 to 10 mm, preferably 3 to 8 mm, and more preferably 5 to 7 mm.

What is claimed is:

1. A chemical analysis slide frame assembly comprising: first and second slide frames each of which has an opening whose area is smaller than the area of a chemical analysis film which said frame assembly is adapted to receive; and a third slide frame disposed between said first and second slide frames, said third slide frame having an opening adapted to receive said chemical analysis film and said third slide frame being shaped so as to substantially prevent the displacement of said chemical analysis film, said third slide frame having a thickness which is equal to or larger than the thickness of said chemical analysis film, and a side wall of the opening in said first slide frame having a small optical reflection factor.

2. The assembly as set forth in claim 1 in which said side wall of the opening in said first slide frame is made dark so as to provide a small optical reflection factor.

3. The assembly as set forth in claim 1 in which said first and third slide frames are formed as a single unit.

4. The assembly as set forth in claim 1 in which said second and third slide frames are formed as a single unit.

5. The assembly as set forth in any one of claims 1 to 4 in which the surface of said first slide frame which is farther from said second slide frame has a small optical reflection factor.

6. The assembly as set forth in any one of claims 1 to 4 in which the surface of said first slide frame which is farther from said second slide frame is made dark so as to provide a small optical reflection factor.

7. The assembly as set forth in any one of claims 1 to 4 in which the side wall of the opening in said first slide frame is an inclined side wall, and one end face of said inclined side wall which is closer to said second slide frame is larger in size than the other end face of said inclined side wall which is farther from said second slide frame.

8. The assembly as set forth in any one of claims 1 to 4 in which the opening of said first slide frame is smaller than the opening of said second slide frame.

9. The assembly as set forth in claim 1 or 2 in which the opening of said first slide frame has the same in configuration and size as the opening of said second slide frame.

10. The assembly as set forth in claim 7 in which the end face of the opening of said first slide frame which is closer to said second slide frame has the same configuration and size as the opening of said second slide frame.

11. The assembly as set forth in claim 7 in which the end face of the opening in said first slide frame which is farther from said second slide frame has the same configuration and size as the opening of said second slide frame.

12. The assembly as set forth in claim 1 or 2 in which a code indicating the kind of a chemical analysis film inserted therein is marked on the surface of said second slide frame which is farther from said first slide frame.

13. The assembly as set forth in claim 12 in which said code is at least one of a protrusion and a recess.

14. The assembly as set forth in claim 12 in which said code is at least one of a protrusion extending from an edge of said second slide frame and a cut formed in said edge of said second slide frame.

15. The assembly as set forth in claim 12 in which said code is a color code marked on a part of the surface of said second slide frame which is farther from said first slide frame.

16. The assembly as set forth in claim 12 in which said code is a color code marked on at least one of the entire surface of said second slide frame which is farther from said first slide frame and said second slide frame which is colored.

17. The assembly as set forth in claim 1 or 2 in which the color of said first slide frame is black.

18. The assembly as set forth in claim 1 or 2 in which the color of said first slide frame is one of matt and lusterless black.

19. The assembly as set forth in claim 1 or 2 in which the surface of said second slide frame which is farther from said first slide frame is formed such that data can be written thereon with writing means.

20. The assembly as set forth in claim 1 or 2 in which the openings in said first and second slide frames are circular.

21. The assembly as set forth in claim 1 or 2 in which the side wall of the opening in said second slide frame has a small optical reflection factor.

22. The assembly as set forth in claim 1 or 2 in which the side wall of the opening in said second slide frame and the surface of said second slide frame which is farther from said first slide frame have a small optical reflection factor.

23. The assembly as set forth in claim 1 or 2 in which the side wall of the opening in said second slide frame and the surface of said second slide frame which is farther from said first slide frame are dark so as to provide a small optical reflection factor.

24. The assembly as set forth in claim 22 in which the color of said second slide frame is black.

25. The assembly as set forth in claim 23 in which the color of said second slide frame is black.

26. The assembly as set forth in claim 22 in which the color of said second slide frame is matt or lusterless black.

27. The assembly as set forth in claim 23 in which the color of said second slide frame is matt or lusterless black.

28. The assembly as set forth in claim 1 or 2 in which said first, second and third slide frames are bonded together.

29. The assembly as set forth in claim 3 in which said first and third slide frames which have been formed as a single unit are bonded to said second slide frame.

30. The assembly as set forth in claim 4 in which said second and third slide frames which have been formed as a single unit are bonded to said first slide frame.

31. The assembly as set forth in claim 29 or 30 in which said bonding is effected using one of ultrasonic waves and an adhesive.

* * * * *